United States Patent
Taraman et al.

(10) Patent No.: US 11,123,366 B1
(45) Date of Patent: Sep. 21, 2021

(54) METHODS, MATERIALS, AND SYSTEMS FOR TREATING INJURIES TO THE CENTRAL NERVOUS SYSTEM USING LIGHT EMITTING NANOPARTICLES

(71) Applicants: Sharief Taraman, Laguna Niguel, CA (US); Spyro Mousses, Scottsdale, AZ (US)

(72) Inventors: Sharief Taraman, Laguna Niguel, CA (US); Spyro Mousses, Scottsdale, AZ (US)

(73) Assignee: Children's Hospital of Orange County, Orange, CA (US)

( * ) Notice: Subject to any disclaimer, the term of this patent is extended or adjusted under 35 U.S.C. 154(b) by 423 days.

(21) Appl. No.: 14/969,110

(22) Filed: Dec. 15, 2015

Related U.S. Application Data

(60) Provisional application No. 62/091,677, filed on Dec. 15, 2014, provisional application No. 62/159,960, filed on May 12, 2015.

(51) Int. Cl.
 *A61N 5/06* (2006.01)
 *A61K 33/24* (2019.01)
 *A61K 41/00* (2020.01)
 *B82Y 5/00* (2011.01)

(52) U.S. Cl.
 CPC .......... *A61K 33/24* (2013.01); *A61K 41/0057* (2013.01); *A61N 5/0601* (2013.01); *A61N 5/0616* (2013.01); *A61N 2005/0659* (2013.01); *B82Y 5/00* (2013.01); *Y10S 977/915* (2013.01)

(58) Field of Classification Search
 CPC ........ A61N 5/06; A61N 5/062; A61N 5/0622; A61N 2005/0658; A61N 2005/0659; A61K 41/0057; A61K 41/10; A61K 41/17; A61K 33/24; A61K 33/242; A61K 33/30
 USPC .......................... 607/88, 89, 92, 100; 128/898
 See application file for complete search history.

(56) References Cited

U.S. PATENT DOCUMENTS

| | | | |
|---|---|---|---|
| 4,966,144 A | 10/1990 | Rochkind et al. | |
| 5,829,448 A | 11/1998 | Fisher | |
| 5,957,960 A | 9/1999 | Chen | |
| 6,235,508 B1 | 5/2001 | Sowemimo-Coker | |
| 6,537,304 B1 | 3/2003 | Oron | |
| 6,918,922 B2 | 7/2005 | Oron | |
| 7,288,108 B2 | 10/2007 | DiMauro et al. | |
| 7,303,578 B2 | 12/2007 | DeTaboada et al. | |
| 7,465,313 B2 | 12/2008 | DiMauro et al. | |
| 8,025,687 B2 | 9/2011 | Streeter | |
| 8,167,921 B2 | 5/2012 | Streeter | |
| 8,262,713 B2 | 9/2012 | Attawia et al. | |
| 8,756,731 B1 | 6/2014 | Huttner | |
| 9,956,425 B2 * | 5/2018 | Peyman ................. | A61N 5/062 |
| 10,195,297 B2 * | 2/2019 | Di Pasqua ............. | A61K 33/26 |
| 2002/0127224 A1 * | 9/2002 | Chen ........................ | B82Y 5/00 424/130.1 |
| 2003/0036199 A1 * | 2/2003 | Bamdad ................. | B82Y 30/00 435/7.23 |
| 2004/0153130 A1 | 8/2004 | Oron | |
| 2006/0216238 A1 * | 9/2006 | Manchester ......... | G01N 33/574 424/9.34 |
| 2007/0179570 A1 | 8/2007 | DeTaboada | |
| 2007/0292353 A1 * | 12/2007 | Levy .................. | A61K 41/0071 424/9.34 |
| 2008/0279946 A1 * | 11/2008 | Hainfeld ................ | A61K 33/24 424/489 |
| 2009/0148502 A1 * | 6/2009 | Pronovost ............... | A61L 15/18 514/1.1 |
| 2009/0297614 A1 * | 12/2009 | Rademacher ........ | A61K 47/549 424/490 |
| 2010/0262115 A1 * | 10/2010 | Madiyalakan ....... | A61K 31/498 604/500 |
| 2013/0013031 A1 | 1/2013 | Ben-Yehuda | |
| 2014/0088367 A1 | 3/2014 | DiMauro | |
| 2015/0147276 A1 * | 5/2015 | Ingber ................ | A61K 41/0014 424/9.5 |
| 2015/0283265 A1 * | 10/2015 | Peyman ............. | A61K 47/6923 424/491 |
| 2017/0316487 A1 * | 11/2017 | Mazed ............... | G06Q 30/0631 |
| 2018/0303667 A1 * | 10/2018 | Peyman ............. | A61F 9/00821 |
| 2020/0246179 A1 * | 8/2020 | Peyman ................. | A61K 9/127 |

OTHER PUBLICATIONS

Fitzgerald et al; 2013; Rev. Neurosci.; 24(2): 205-226 "Red/near-infrared irradiation therapy for treatment of central nervous system injuries and disorders".

Chen et al.; 2006; J. Nanoscience and Nanotechnology; 6:157-161 "Sonochemical Fabrication and Characterization of Ceria (CeO2)Nanowires".

Kim et al. 2007; J Am. Chem. Soc.; 129:2669-2675 "Organically Modified Silica Nanoparticles Co-encapsulating Photosensitizing Drug and Aggregation-Enhanced Two-Photon Absorbing Fluorescent Dye Aggregates for Two-Photon Photodynamic Therapy".

Walling et al. 2009; Int. J. Mol. Sc. 10:441-491; "Quantum Dots for Live Cell and In Vivo Imaging".

Murray et al., 1993 J. Am. Chem. SOG.; 115:8706-8715 "Synthesis and Characterization of Nearly Monodisperse CdE (E=S, Se, Te) Semiconductor Nanocrystallites".

Hines and Guyot-Sionnest; 1998 J. Phys. Chem. B; 102:3655-3657 Bright UV-Blue Luminescent Colloidal ZnSe Nanocrystals.

Yu and Peng; 2002; Angew. Chem. Int. Ed. 41:2368-2370 "Formation of High-Quality CdS and Other II ±VI Semiconductor Nanocrystals in Noncoordinating Solvents:T unable Reactivity of Monomers".

Norris et al.; 2001; Nano Letters; 1:3-7 "High-Quality Manganese-Doped ZnSe Nanocrystals".

Krueger et al.; 2005; Anal. Chem. 77:3511-3515 "Characterization of Nanocrystalline CdSe by Size Exclusion Chromatography".

Peng and Peng; 2001; J. Am. Chem. Soc. 123:183-184 "Formation of High-Quality CdTe, CdSe, and CdS Nanocrystals Using CdO as Precursor".

(Continued)

*Primary Examiner* — Ahmed M Farah

(57) ABSTRACT

The present invention relates to the use of light-emitting, water soluble nanoparticles in the treatment of disorders of the central nervous system.

8 Claims, No Drawings

(56) References Cited

OTHER PUBLICATIONS

Micic et al.; 1995; J. Phys. Chem.; 99:7754-7759 "Synthesis and Characterization of InP, Gap, and GaInP2 Quantum Dots".
Murray et al.; 2001; IBM J. Res. & Dev.; 45:47-56 "Colloidal synthesis of nanocrystals and nanocrystal superlattices".
Du et al.: 2002; Nano Letters; 2:1321-1324 "Optical Properties of Colloidal PbSe Nanocrystals".
Pietryga et al; 2004; J. Am. Chem. Soc. 126:11752-11753 "Pushing the Band Gap Envelope: Mid-Infrared Emitting Colloidal PbSe Quantum Dots".
Kovalenko et al.; 2007; J. Am. Chem. Soc. 127:11354-11355 "SnTe Nanocrystals: A New Example of Narrow-Gap Semiconductor Quantum Dots".
Bruchez et al.; 1998; Science 281:2013-2015 "Semiconductor Nanocrystals as Fluorescent Biological Labels".
Hines and Guyot-Sionnest; 1996 J. Phys. Chem. 100:468-471 "Synthesis and Characterization of Strongly Luminescing ZnS-Capped CdSe Nanocrystals".
Danek et al.; 1996; Chem. Mater. 8:173-180 "Synthesis of Luminescent Thin-Film CdSe/ZnSe Quantum Dot Composites Using CdSe Quantum Dots Passivated with an Overlayer of ZnSe".
Dabbousi et al.; 1997; 1996 J. Phys. Chem. B 101:9463-9475 "(CdSe)ZnS Core-Shell Quantum Dots: Synthesis and Characterization of a Size Series of Highly Luminescent lanocrystallites".
Peng et al.; 1997; J. Am. Chem. Soc. 119:7019-7029 "Epitaxial Growth of Highly Luminescent CdSe/CdS Core/Shell Nanocrystals with Photostability and Electronic Accessibility".
Talapin et al.; 2001; Nano Letters; 1:207-211 "Highly Luminescent Monodisperse CdSe and CdSe/ZnS Nanocrystals Synthesized in a Hexadecylamine-Trioctylphosphine Oxide-Trioctylphospine Mixture".
Mattoussi et al.; 2000; J. Am. Chem. Soc.; 122:12142-1150 "Self-Assembly of CdSe—ZnS Quantum Dot Bioconjugates Using an Engineered Recombinant Protein".
Gao et al.; 2002; J. Biomedical Optics; 7:532-537 "Quantum-dot nanocrystals for ultrasensitive biological labeling and multicolor optical encoding".
Pinaud et al.; 2004; J. Am. Chem. Soc. 126:6115-6123 "Bioactivation and Cell Targeting of Semiconductor CdSe/ZnS Nanocrystals with Phytochelatin-Related Peptides".
Mattoussi et al.; 2001; Phys. Stat. Sol. (b) 224:277-283 "Bioconjugation of Highly Luminescent Colloidal CdSe—ZnS Quantum Dots with an Engineered Two-Domain Recombinant Protein".
Sukhanova et al.; 2002; Laboratory Investigation; 82:1259-1261 "Highly Stable Fluorescent Nanocrystals as a Novel Class of Labels for Immunohistochemical Analysis of Paraffin-Embedded Tissue Sections".
Chan and Nie; 1998; Science 281: 2016-2018 "Quantum Dot Bioconjugates for Ultrasensitive Nonisotopic Detection".
Chen and Gerion; 2004; Nano Letters 4:1827-1832 "Fluorescent CdSe/ZnS Nanocrystal-Peptide Conjugates for Long-term, Nontoxic Imaging and Nuclear Targeting in Living Cells".
Ryman-Rasmussen et al.; 2007; J. Invest. Dermatology; 127:143-153 "Surface Coatings Determine Cytotoxicity and Irritation Potential of Quantum Dot Nanoparticles in Epidermal Keratinocytes".
Duan and Nie; 2006; J. Am. Chem. Soc.; 129:3333-3338 "Cell-Penetrating Quantum Dots Based on Multivalent and Endosome-Disrupting Surface Coatings".
Akerman et al.; 2002; PNAS; 99:12617-12621 "Nanocrystal targeting in vivo".
Gerion et al. 2001; J. Phys. Chem. B 105:8861-8871 "Synthesis and Properties of Biocompatible Water-Soluble Silica-Coated CdSe/ZnS Semiconductor Quantum Dots".
Dubertret et al.; 2002 Science 298:1759-1762 "In Vivo Imaging of Quantum Dots Encapsulated in Phospholipid Micelles".
Larson et al. 2003; Science 300:1434-1436 "Water-Soluble Quantum Dots for Multiphoton Fluorescence Imaging in Vivo".
Wu et al; 2003; Nature Biotechnology 21:41-46 "Immunofluorescent labeling of cancer marker Her2 and other cellular targets with semiconductor quantum dots".
Kim et al.; 2004; Nature Biotechnology; 22:93-97 "Near-infrared fluorescent type II quantum dots for sentinel lymph node mapping".
Gussin et al.; 2006; J. Am. Chem. Soc. 128:15701-15713 "Binding of Muscimol-Conjugated Quantum Dots to GABAC Receptors".
Schroeder et al.; 2007; J. Controlled Release 124:28-34 "Folate-mediated tumor cell uptake of quantum dots entrapped in lipid nanoparticles".
Jayagopal et al.; 2007; Bioconjugate Chem. 18:1424-1433 "Surface Engineering of Quantum Dots for In ViWo Vascular Imaging".
Jin et al.; 2008; Chem. Mater. 20:4411-4419 "Silica Nanoparticles with Continuously Tunable Sizes: Synthesis and Size Effects on Cellular Contrast Imaging".
Park et al. 2008; Adv. Mater. 20:1630-1635 "Magnetic Iron Oxide Nanoworms for Tumor Targeting and Imaging".
Wang et al.; 2008; Gold Bulletin; 41:36-40 "Gold Nanoparticle-based Optical Probes for Target-Responsive DNA Structures".
Nakamura et al; 2007; Anal. Chem. 79:6507-6514 "Synthesis, Characterization, and Biological Applications of Multifluorescent Silica Nanoparticles".
Gong et al.; 2006; Analytica Chimica Acta 564:151-157 "Novel dye-embedded core-shell nanoparticles as surface-enhanced Raman scattering tags for immunoassay".
Ow et al.; 2005; Nano Letters 5:113-117 "Bright and Stable Core-Shell Fluorescent Silica Nanoparticles".
Doering and Nie; 2003; Anal. Chem. 75:6171-6176 "Spectroscopic Tags Using Dye-Embedded Nanoparticles and Surface-Enhanced Raman Scattering".
Abdukayum et al.; 2013; J. Am. Chem. Soc. 135:14125-14133 "Functional Near Infrared-Emitting Cr3+/Pr3+ Co-Doped Zinc Gallogermanate Persistent Luminescent Nanoparticles with Superlong Afterglow for in Vivo Targeted Bioimaging".
Mikulec; 1999; Massachusetts Institute of Technology Thesis for the Degree of Doctor of Philosophy "Semiconductor Nanocrystal Colloids: Manganese Doped Cadmium Selenide, (Core)Shell Composites for Biological Labeling, and Highly Fluorescent Cadmium Telluride".

\* cited by examiner

METHODS, MATERIALS, AND SYSTEMS FOR TREATING INJURIES TO THE CENTRAL NERVOUS SYSTEM USING LIGHT EMITTING NANOPARTICLES

FIELD OF THE INVENTION

This invention relates to the use of light-emitting nanoparticles in the treatment of disorders of the central nervous system.

BACKGROUND OF THE INVENTION

A recent exciting advance in the treatment of disease generally and central nervous systems disorders specifically involves the use of red or near-infrared irradiation therapy. Fitzgerald et al Rev. Neurosci. 2013; 24(2): 205-226 have recently provided an excellent review of the use of irradiation in the red/near-infrared spectrum (R/NIR, 630-1000 nm) as it has been used to treat a wide range of clinical conditions, including disorders of the central nervous system (CNS). This review is incorporated herein by reference in its entirety.

Therapeutic use of irradiation at the clinically relevant wavelengths is characterized by low energy densities and is called R/NIR-IT. It is distinct from high-energy ablative or thermocoagulatory laser treatments, or light dependent imaging techniques. Improvements following R/NIR-IT have been observed in a wide array of clinical conditions, including wound healing (Yu et al., 1997; Whelan et al., 2001, 2003), oral mucositis (Eells et al., 2004), cardial infarct size (Oron et al., 2001) and renal and hepatic complications during diabetes (Lim et al., 2009, 2010). Beneficial effects have been reported following retinal degeneration (Natoli et al., 2010; Albarracin and Valter 2012b), central nervous system (CNS) injury (Byrnes et al., 2005; Fitzgerald et al., 2010), stroke (Lapchak et al., 2007), peripheral nerve damage (Rochkind et al., 2009; Ishiguro et al., 2010) and for restless leg syndrome (Mitchell et al., 2011). All of the foregoing publications are incorporated herein by reference in their entirety.

Variables in treatment include irradiation sources (prior to the instant invention, limited to laser or light-emitting diode), mode of delivery (pulsed or continuous), stimulation wavelength (630, 670, 780, 810, 830, 880 or 904 nm), total dose (i.e., joules of irradiation per unit area), rate of delivery of the irradiation energy [watts per unit area (note: watts=joules °ø time), also referred to as fluence], duration (length of exposure timing (pre- or post-insult), depth of a target cell continuous wave or pulsed mode, pulse parameters and frequency of treatment (Quirk and Whelan, 2011). (See also, e.g., Karu I T, Low-Power Laser Therapy", in Biomedical Photonics Handbook, Vo-Dinh T. Ed., CRC Press, Boca Raton, Fla., pp. 48-1 to 48-25, (2003) incorporated herein by reference).

U.S. Pat. No. 7,288,108 discloses an implantable diode that emits red light onto the substantia nigra as a treatment for Parkinson's Disease. The red light has a wavelength of between about 650 nm and about 1000 nm.

US 20140088367 discloses the use of red or near infrared light upon neurons of the lumbar plexus that are in distress due to retraction-induced ischemia. In that disclosure the surgeon may protect nerves made ischemic in the surgery by: a) making an incision in a patient, b) inserting an access device into the patient through the incision to at least partially create a path to a spine of the patient, and c) irradiating nervous tissue adjacent the path with an amount of NIR or red light effective to provide neuroprotection.

U.S. Pat. No. 7,465,313 B2 discloses red light-emitting implants for treating degenerative disc disease.

U.S. Pat. No. 8,262,713 B2 discloses red light implants for delivering red light to spinal implants to enhance osteointegration and for treating osteoporosis.

U.S. Pat. No. 4,966,144 discloses a method of inducing functional regeneration of nerve fibers of an injured sight of the spinal cord (or using grafts of peripheral nerves which were placed into the injured sight) by a light source which generates light at a wavelength of 330-1200 nm.

U.S. Pat. Nos. 6,537,304 and 6,918,922 disclose an apparatus for treatment of an ischemic region of brain cells in a cranium, comprising a skull covering adapted to cover at least part of the cranium, at least one guide attached to the skull covering, and a laser source which is operative to direct a laser beam through at least one guide into the cranium. The guide may include an optic fiber or a waveguide.

U.S. Pat. No. 7,303,578 discloses a therapy apparatus for treating a patient's brain. The therapy apparatus includes a light source having an output emission area positioned to irradiate a portion of the brain. The therapy apparatus further includes an element interposed between the light source and the patient's scalp. The element is adapted to inhibit temperature increases at the scalp caused by the light.

US 20070179570 discloses a wearable device and method for providing phototherapy to the brain.

U.S. Pat. Nos. 8,025,687, 8,167,921, US20090216301, US20110245897, US20120010685, and U.S. Pat. No. 7,534,255 all disclose aspects and therapeutic methods for enhancing neurologic function such as may be desired in individuals having motor and/or cognitive impairment, including that resulting from Alzheimer's disease, dementia, head trauma, mental disease such as depression, stroke and neurodegeneration, as well as in healthy individuals. The methods include delivering light energy having a wavelength in the visible to near-infrared wavelength range to a target area of the brain. In one embodiment, progenitor cells are treated using light energy and implanted into the central nervous system of a patient.

US 20040153130 discloses therapeutic methods for treating or inhibiting a neuromuscular disease or condition, including muscular dystrophy, in a subject in need thereof are described, the methods including applying to muscle tissue of the subject a muscular dystrophy effective amount of electromagnetic energy having a wavelength in the visible to near-infrared wavelength.

U.S. Pat. No. 8,756,731 discloses a phototherapy infant swaddling blanket for treating jaundice.

U.S. Pat. No. 6,596,016 discloses a phototherapy of jaundiced newborns using garments containing semiconductor light-emitting devices.

US 20130013031 discloses a swallowable suitable for providing phototherapy to a region of a patient's gastrointestinal (GI) tract, the capsule comprising one or more light sources emitting in the visible and/or NIR ranges and optical elements for shaping the light beam produced by said light sources, such that said light source(s) and said optical elements are capable of delivering an effective therapeutic dose to a target site within the GI tract. The present invention further provides a method for intraluminal phototherapy of the gastrointestinal tract using a swallowable capsule as described hereinabove.

U.S. Pat. No. 5,829,448 describes sequential and simultaneous two photon excitation of photo-agents using irradiation with low energy photons such as infrared or near infrared light. A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest. The present invention solves this problem using nanoparticles to deliver light to within close proximity to the affected tissue deep within the CNS.

Chen et al., J. Nanosci, and Nanotech., 6:1 159-1 166 (2006); Kim et al., JACS, 129:2669-2675 (2007); U.S. 2002/0127224; and U.S. Pat. No. 4,979,935 each describe methods for treatment using various types of energy activation of agents within a subject.

U.S. Pat. No. 5,957,960 discloses a two-photon excitation device for administering a photodynamic therapy to a treatment site within a patient's body using light having an infrared or near infrared waveband.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

U.S. published application 2002/0127224 discloses a method for a photodynamic therapy comprising administering light-emitting nanoparticles and a photoactivatable agent, which may be activated by the light re-emitted from the nanoparticles via a two-photon activation event. An initiation energy source is usually a light emitting diode, laser, incandescent lamp, or halogen light, which emits light having a wavelength ranging from 350 to 1,100 nm. The initiation energy is absorbed by the nanoparticles. The nanoparticles, in turn, re-emit light having a wavelength from 500 to 1 100 nm, wherein the re-emitted energy activates the photoactivatable agent.

Kim et al., (JACS, 129:2669-75, Feb. 9, 2007) disclose indirect excitation of a photosensitizing unit (energy acceptor) through fluorescence resonance energy transfer (FRET) from the two-photon absorbing dye unit (energy donor) within an energy range corresponding to 300-850 nm.

The Problem: Penetration of Irradiation into the Human Brain

The extent to which R/NIR irradiation can penetrate the brain is a key determinant of potential efficacy for existing phototherapies. A number of factors affect R/NIR irradiation penetration of tissue. Haemoglobin and water are major chromophores, that absorb irradiation (Sterenborg et al., 1989), thus the extent of R/NIR irradiation penetration will vary according to vascularization and fluid balance. Optimal penetration within biological tissues occurs within a therapeutic or optical window with a wavelength range of 600-1000 nm (Parrish, 1981). The effective penetration depth of a given wavelength of irradiation is dependent upon the optical properties of the tissue, i.e., absorption and scattering (Cheong et al., 1990). Irradiation in the range of 600-1000 nm penetrates tissue because scattering by tissue inhomogeneities is dominant (Profio, 1989). Scattering increases the distance travelled by photons, thus diffusing the propagating irradiation. Absorption occurs predominantly by chromophores such as melanin and haemoglobin at short wavelengths and water and cytochrome c oxidase, a photoacceptor within the mitochondrial electron transport chain, at longer wavelengths (Karu, 1989; Sutherland, 2002).

Few studies have directly measured the penetration of R/NIR irradiation in intact animals and those that have, focused on rats. (Fitzgerald et al., 2010). Whether or not the extremely low level of irradiation reaching the center of the brain is effective for irradiation therapy of CNS injury or disease remains to be definitively determined. The present invention solves this problem by delivering light into close proximity with the affected tissues using light emitting nanoparticles such as quantum dots. A quantum dot (OD) is a nanocrystal made of semiconductor materials that are small enough to exhibit quantum mechanical properties.

DETAILED DESCRIPTION OF THE INVENTION

In certain embodiments the present invention includes the treatment of a variety of central nervous system disorders and injuries using suitable light-emitting nanoparticles including quantum dots (QDs). Quantum dots are semiconductor nanocrystals which generally fall within the 2-10 nanometer size range and possess size controllable, optical and electrical properties. Other nanoparticles, such as Cr3+/Pr3+ co-doped zinc gallogermanate, gold nanoparticles, fluorescent dye-doped silica nanoparticles, Raman-active dye-embedded nanoparticles, and "nanoworms" may also be used in certain embodiments of the present invention. Like quantum dots, these nanoparticles may be conjugated to antibodies, DNA, or other biomolecules for use in the invention.

In certain embodiments the quantum dot semiconductor core is coated with a shell material, comprised of a second semiconductor material. The core/shell quantum dots are coated for biocompatibility and solubility. Quantum dots have been estimated to be up to 20 times brighter and 100 times more stable than traditional fluorescent reporters. Chan and Nie, Quantum Dot Bioconjugates for Ultrasensitive Nonisotopic Detection. Science 1998, 281, 2016-2018.

Synthesis

Walling, et al. in Quantum Dots for Live Cell and In Vivo Imaging. Int. J. Mol. Sci. 2009, 10, 441-491; doi:10.3390/ijms10020441 provide an excellent review and summarization of QD synthesis, disclosed below and incorporated herein in its entirety.

Quantum dot cores are composed of semiconductors of group II-VI (CdSe, CdS, CdTe), group IV-VI (PbS, PbSe, PbTe, SnTe), and group III-V (InP), or any other combination with extremely narrow bandgaps, the most common being CdSe. Generally, organometallic liquid precursors are injected into hot (290°-350° C.) coordinating solvents, such as trioctylphosphine oxide (TOPO) and trioctylphosphine (TOP). Coordinating solvents stabilize the bulk semiconductors and prevent aggregation as the quantum dots grow. After the desired size and optical properties are achieved (based on size), aliquots are removed from the reaction mixture, cooled, and purified. Purification steps, such as precipitation in alcohol, are performed and can serve as size exclusion steps to ensure uniformity. The uniformity and average nanocrystal size can be affected by temperature differences of less than 1° C. If suitable conditions for injection temperature and growth time are maintained during synthesis, separate size-selection steps are not necessary to achieve a narrow size distribution. Nanoparticles synthesized in this manner result in the semiconductor core surrounded by TOPO, in a nonpolar solvent such as chloroform.

The synthesis methodology to produce quantum dots with customizable properties is now well known, straightforward and reproducible. Through the many modifiable parameters involved (precursors, solvents, reagent concentrations, temperature, growth time, etc.), quantum dots of varying core compositions and sizes can be produced, resulting in specific synthetic methods that correlate directly to the desired optical properties. Common experimental variations include the alteration of the core composition by the use of different metallic precursors, or additional reagents in the solvent mixture, such as hexadecylamine (HDA), which improves monodispersity and eliminates size exclusion steps. Ultimately, to fabricate quantum dots of varying particle size (and thus varying emission wavelengths) in a single reaction, synthesis can be carried out in non-coordinating solvents, with aliquots quenched at time points throughout the reaction. Each quenched aliquot results in a specific diameter of nanoparticle with uniform distribution. See also:

Murray et al., Synthesis and Characterization of Nearly Monodisperse CdE (E=sulfur, selenium, tellurium) Semiconductor Nanocrystallites. J. Am. Chem. Soc. 1993, 115, 8706-8715.

Hines and Guyot-Sionnest, Bright UV-Blue Luminescent Colloidal ZnSe Nanocrystals. J. Phys. Chem. B 1998, 102, 3655-3657.

Yu and Peng, Formation of High-Quality CdS and Other II-VI Semiconductor Nanocrystals in Noncoordinating Solvents: Tunable Reactivity of Monomers. Angew. Chemie 2002, 41, 2368-2371.

Norris et al., High-Quality Manganese-Doped ZnSe Nanocrystals. Nano Lett. 2001, 1, 3-7.

Krueger et al., Characterization of Nanocrystalline CdSe by Size Exclusion Chromatography. Anal. Chem. 2005, 77, 3511-3115.

Peng and Peng, Formation of High-Quality CdTe, CdSe, and CdS Nanocrystals Using CdO as Precursor. J. Am. Chem. Soc. 2001, 123, 183-184.

Micic et al., Synthesis and Characterization of InP, GaP, and GaInP2 Quantum Dots. J. Phys. Chem. 1995, 99, 7754-7759.

Murray et al., Colloidal Synthesis of Nanocrystals and Nanocrystal Superlattices. IBM J. Res. Dev. 2001, 45, 47.

Du et al., Optical Properties of Colloidal PbSe Nanocrystals. Nano Lett. 2002, 2, 1321-1324.

Pietryga et al., Pushing the Band Gap Envelope: Mid-Infrared Emitting Colloidal PbSe Quantum Dots. J. Am. Chem. Soc. 2004, 126, 11752-11753.

Kovalenko et al., SnTe Nanocrystals: A New Example of Narrow-Gap Semiconductor Quantum Dots. J. Am. Chem. Soc. 2007, 129, 11354-11355.

Shell Growth and Surface Modification

The semiconductor core material may be protected from degradation and oxidation in order to maintain and optimize quantum dot performance. Both shell growth and surface modification enhance stability and increase photoluminescence of the core. As mentioned previously, shell growth provides protection by coating or capping the core with a thin layer of a second semiconductor material with a higher band gap. The semiconductor shells are also inorganic in nature, commonly employing compounds such as zinc sulfide or zinc selenide (ZnS, ZnSe). Surface protection can also be achieved through modification of the core, which is carried out in organic solvents, such as alkylamines, but including a semiconductor shell layer is most common protection method. Semiconductor shells are grown epitaxially by addition of shell precursors drop-wise into a crude nanocrystal mixture at a temperature below that of core synthesis. The reduced temperature facilitates shell growth by capping the pre-existing nanoparticle cores instead of initiating a separate nucleation of shell precursors. Shell thickness is controlled by varying the growth temperature and the concentration and rate at which reagents are added. If the shell growth temperature is too close to that of the core synthesis temperature, core seeds will continue to grow and negatively effect (broaden) the size distribution. Conversely, if the shell growth proceeds at lower temperatures, the crystallinity of the shell is decreased, leading to imperfect passivation of the core surface, among other problems. The concentration of shell precursors and their rate of addition are crucial to promote heterogeneous growth. Shell formation and thickness is measured in a series of discrete monolayers, which for ZnS shells are ~3.0-3.5 Å thick, but again vary based on the shell composition and its growth method. The number of shell monolayers is controllable, but generally does not exceed more than five. Even when strict precautions are taken, some shell precursor elements may nucleate separately and size selection steps are often required to ensure the quality of the final product. The overall process of epitaxial shell growth results in the formation of core/shell nanocrystals surrounded by the coordinating solvent such as TOPO, used during growth, dispersed in a nonpolar solvent.

In contrast to shell growth, direct surface modifications of the core using organic solvents occur through surface exchange reactions. For example, surface exchange can be performed by mixing crude TOPO-coated nanocrystals with an organic solvent, such as an alkylamine. The alkylamine acts as a competing capping group and displaces the TOPO from the core surface. This exchange reaction can take place in a single step, or can be done as a series of steps. With the single step process, the extent of coverage is determined by the length of exposure to the capping group and is measured at the conclusion of the process. The benefit of the multiple step method is more reliable control over the extent of coating. When coating in a stepwise manner, optical measurements taken at each step in the process can measure the positive effect on quantum yield. Core modification by surface exchange reactions is generally reversible, and because of the nature of the capping material, this type of organically-capped quantum dot cores cannot be employed in biological applications.

The most common cap for CdSe nanocrystals is a ZnS shell. The ZnS shell does not incorporate into the core or alter the core structure, but has been shown to increase the quantum yield of the CdSe core by 50-66%. Slightly smaller increases have been observed with organic alkylamine caps, demonstrating an increase in the core quantum yield by up to 50%. Both shells and caps also provide important protection, contributing to the: stability of the core against degradation and photobleaching. Finally, the addition of a shell or cap material can also provide terminal functional sites to provide for further derivatization, such as aqueous solubilization.

See also:

Bruchez et al., Semiconductor Nanocrystals as Fluorescent Biological Labels. Science 1998, 281, 2013-2016.

Murray et al., Synthesis and Characterization of Nearly Monodisperse CdE (E=sulfur, selenium, tellurium) Semiconductor Nanocrystallites. J. Am. Chem. Soc, 1993, 115, 8706-8715.

Hines and Guyot-Sionnest, Synthesis and Characterization of Strongly Luminescing ZnSCapped CdSe Nanocrystals. J. Phys. Chem. 1996, 100, 468-471.

Danek et al., Synthesis of Luminescent Thin-Film CdSe/ZnSe Quantum Dot Composites Using CdSe Quantum Dots Passivated with an Overlayer of ZnSe. Chem. Mater. 1996, 8, 173-180.

Dabbousi et al., (CdSe)ZnS Core-Shell Quantum Dots: Synthesis and Characterization of a Size Series of Highly Luminescent Nanocrystallites. J. Phys. Chem. B 1997, 101, 9463-9475.

Peng et al., Epitaxial Growth of Highly Luminescent CdSe/CdS Core/Shell Nanocrystals with Photostability and Electronic Accessibility. J. Am. Chem. Soc. 1997, 119, 7019-7029.

Talapin et al., Highly Luminescent Monodisperse CdSe and CdSe/ZnS Nanocrystals Synthesized in a Hexadecylamine-Trioctylphosphine Oxide-Trioctylphospine Mixture. Nano Lett. 2001, 1, 207-211.

Aqueous Solubilization

The inorganic core-shell semiconductor nanoparticles, once prepared, are soluble in nonpolar solvents only. To have utility in biological applications, nanoparticles must be soluble in aqueous solutions and require surface modifications to achieve biocompatibility. Two general approaches have been used to achieve aqueous solubility: surface ligand exchange and amphiphilic polymer coatings. A wide range of molecules are available to serve as surface coatings to solubilize quantum dots, including thiolate ligands, silica, and various polymers. See Walling et al., supra and Bruchez et al., Semiconductor Nanocrystals as Fluorescent Biological Labels. Science 1998, 281, 2013-2016.

Surface Ligand Exchange

In certain embodiments of the invention, two different surface ligand exchange approaches may be used for solubilization. The first method involves exchanging the coordinating ligands (e.g. TOPO) on the quantum dot shell surface. The exchange process is similar to surface exchange reactions of the core described previously, and optimally results in the addition of a heterobifunctional ligand. A bifunctional ligand employs a hydrophobic end to displace the TOPO from the quantum dot, while a hydrophilic end extends out into solution, aiding in solubility. Thiol groups are a common functionality employed to link to the shell surface, but this functional group can detach from the quantum dot surface in a reversible fashion. Successful thiol group attachment has been achieved using mercapto-compounds, cysteine residues, or chemically reduced proteins. In each of these cases, a carboxyl group or protein residues served as the hydrophilic tail, extending out into solution and allowing the quantum dots to be soluble in an aqueous environment.

For more details see also:

Mattoussi et al., Self-Assembly of CdSe—ZnS Quantum Dot Bioconjugates Using an Engineered Recombinant Protein. J. Am. Chem. Soc. 2000, 122, 12142-12150.

Gao et al., Quantum-dot Nanocrystals for Ultrasensitive Biological Labeling and Multicolor Optical Encoding. J. Biomed. Opt. 2002, 7, 532-537.

Pinaud et al., Bioactivation and Cell Targeting of Semiconductor CdSe/ZnS Nanocrystals with Phytochelatin-Related Peptides. J. Am. Chem. Soc. 2004, 126, 6115-6123.

Mattoussi et al., Bioconjugation of Highly Luminescent Colloidal CdSe—ZnS Quantum Dots with an Engineered Two-Domain Recombinant Protein. Phys. Status Solidi B. 2001, 224, 277-283.

Sukhanova et al., Highly Stable Fluorescent Nanocrystals as a Novel Class of Labels for Immunohistochemical Analysis of Paraffin-Embedded Tissue Sections. Lab. Invest. 2002, 82, 1259-1261.

A second surface exchange method involves silane derivatives, used to displace the coordinating ligand on the quantum dot surface, and eventually resulting a layer of silica around the quantum dot. The reaction conditions, in particular reaction time, contribute to the thickness of the silica shell. Silica shell growth around a core/shell quantum dot involves mixing the quantum dots with a compound at basic pH over several days while continually heating, cooling, and washing the solution. Silica shell growth requires multiple purification steps. Compared with the synthesis of mercaptoacetic acid-capped quantum dots, encapsulating quantum dots with a silica shell is more complicated, but the difficult nature of synthesis is countered by its advantages. This latter approach is advantageous because quantum dots coated with silica are more stable due to the high degree of crosslinking between the silane molecules. This extensive cross-linking ensures solubility even if some thiol groups are lost. An additional advantage of using silica shell coatings is that the procedures do not change if a different type of siloxane is used. Ultimately, using either surface ligand exchange approach for solubilization leaves quantum dots susceptible to aggregation and precipitation in biological buffers, and may require additional efforts to reduce or minimize aggregation. For more details see also:

Chan and Nie, Quantum Dot Bioconjugates for Ultrasensitive Nonisotopic Detection. Science 1998, 281, 2016-2018.

Chen and Gerion, Fluorescent CdSe/ZnS Nanocrystal-Peptide Conjugates for Long-term, Nontoxic Imaging and Nuclear Targeting in Living Cells. Nano Lett. 2004, 4, 1827-1832.

Ryman-Rasmussen et al., Surface Coatings Determine Cytotoxicity and Irritation Potential of Quantum Dot Nanoparticles in Epidermal Keratinocytes. J. Invest. Dermatol. 2006, 127, 143-153.

Duan and Nie, Cell-Penetrating Quantum Dots Based on Multivalent and Endosome-Disrupting Surface Coatings. J. Am. Chem. Soc. 2007, 129, 3333-3338.

Akerman et al., Nanocrystal Targeting In Vivo. Proc. Natl. Acad. Sci. USA 2002, 99, 12617-12621.

Gerion et al., Synthesis and Properties of Biocompatible Water-Soluble Silica-Coated CdSe/ZnS Semiconductor Quantum Dots. J. Phys. Chem. B 2001, 105, 8861-8871.

Amphiphilic Polymer Coatings

In other embodiments of the invention, core semiconductor quantum dots can be coated with an amphiphilic polymer, such as octylamine-modified polyacrylic acid. This approach utilizes the nonpolar quantum dot shell for interaction with the hydrophobic portion of the polymer, allowing the hydrophilic portion of the polymer to increase solubility. Growing an amphiphilic polymer shell around quantum dots is similar to coating with silica, but instead of forming the shell by displacing the TOP© molecules left on the surface during synthesis, the amphiphilic polymer takes advantage of the hydrophobic nature of the coordinating ligands.

See also:

Dubertret et al., In Vivo Imaging of Quantum Dots Encapsulated in Phospholipid Micelles. Science 2002, 298, 1759-1762.

Larson et al., Water-Soluble Quantum Dots for Multiphoton Fluorescence Imaging In Vivo. Science 2003, 300, 1434-1436.

Wu et al., Immunofluorescent Labeling of Cancer Marker Her2 and Other Cellular Targets with Semiconductor Quantum Dots. Nat. Biotechnol. 2003, 21, 41-46.

Kim et al, Nature Biotechnology, 22 (2004) disclose suitable nanoparticles they obtained from Li-Cor. These are IRDye78-CA. These NIR CdTe(CdSe) core(shell) type II QDs may be prepared as follows. All procedures should be performed under an inert atmosphere, unless otherwise specified.

Gussin et al., Binding of Muscimol-Conjugated Quantum Dots to GABA Receptors. J. Am. Chem. Soc. 2006, 128, 15701-15713, discloses the use of polymers.

A specific type of amphiphilic polymer, PEG-incorporated phospholipid micelles, has been used to encapsulate quantum dots for in vivo cell-lineage tracking. Dubertret et al., In Vivo Imaging of Quantum Dots Encapsulated in Phospholipid Micelles. Science 2002 298, 1759-1762.

Toxicity

Although quantum dots exhibit numerous advantageous optical properties, inorganic semiconductor materials are generally toxic to living systems, limiting their use in biological systems. Therefore, numerous methods have been developed to modify quantum dots to limit cytotoxicity such as surface coatings which have been developed in an effort to minimize toxicity.

Quantum dot toxicity has been extensively examined. Toxicity has been related to oxidation of the nanoparticle core/shell material, leading to the release of free cadmium. The nature of the surface coatings obviously plays an important part of this process. Walling et al., supra.

As outlined by Kim, et al, Nature Biotechnology, Volume 22 (2004), despite being composed of potentially toxic materials, the low dose and chemical form of the materials are such that the overall toxicity is low. For example, 400 pmol of NIR QDs corresponds to approximately 9.9 µg/kg, 7.3 µg/kg, 2.4 µg/kg and 4.1 µg/kg of cadmium, telluride, selenide and alkyl phosphines; respectively. In the case of cadmium, for which the most data are available, this dose is approximately 300 times lower than the daily dose that causes renal toxicity in rats after 6 weeks of continuous exposure in drinking water. Moreover, a treatment for elemental cadmium poisoning in humans is the infusion of elemental selenium to produce less toxic cadmium selenide salts. Kim et al saw no change in electrocardiographic and pulse oximetry measurements during large-animal surgery and for several hours thereafter.

Kim et al suggest simple strategies for minimizing the potential for toxicity. The first is simply to increase the fluence rate and proportionally lower the injected NIR QD dose. The photobleaching data suggest that at least a 100-fold lower dose could be used. The second is that type II structures permit combinations of nontoxic materials, which would otherwise emit in the visible light range, to emit in the NIR. Finally, during a typical SLN mapping procedure, the tumor (site of QD injection) and SLN are both resected, thus minimizing exposure to the QD materials. Future studies should address these important issues and the use of type II QD structures in other biomedical assay and imaging applications.

Quantum dots can target specific receptors in vivo [Schroeder et al., Folate-mediated Tumor Cell Uptake of Quantum Dots Entrapped in Lipid Nanoparticles. J. Control. Release 2007, 124, 28-34]. Quantum dots were conjugated to folate, a critical nutrient necessary for rapid growth and cell division, to perform assays targeting the folate-specific receptor. TOPO-coated quantum dots (CdSe) were prepared in phospholipid micelles and assessed in animal studies. The folate-quantum dot conjugates were specifically detected at the folate receptors in mouse lymphoma cells after incubation for two hours and was highly specific in its targeting.

Antibody-quantum dot conjugates were also used to optimize circulation times and provide specificity for in vivo applications [Jayagopal et al., Surface Engineering of Quantum Dots for In Vivo Vascular Imaging. Bioconjugate Chem. 2007, 18, 1424-1433]. These conjugates were used for standard microscopy determinations, flow cytometry assays, and in vivo imaging. The quantum dot conjugates targeted cell adhesion molecules related to retinal vasculature in rats in a multiplexed fashion using a single excitation source. The researchers employed a PEG crosslinking scheme to link the antibodies and were able to discriminate between different cell adhesion molecules by conjugating specific monoclonal antibodies to quantum dots. This work demonstrated noninvasive, in vivo imaging of the retinal vasculature, while providing the spatial resolution down to the level of single cells. The fluorescence intensities increased within 30 minutes, whereas non-specifically labeled quantum dots and the control showed no fluorescence localization in the vasculature.

In certain aspects of the present invention, target-specific quantum dots can be used to deliver light to specific tissues or cells within the CNS, reducing the dose required and thus any potential toxicity.

Additional Nanoparticles

Silica nanoparticles, magnetic iron oxide "nanoworms", and gold nanoparticles can all be coated and used in certain aspects of the present invention in a manner very similar to quantum dots. For further information on useful nanoparticles according to the invention see:

Jin et al., Silica Nanoparticles with Continuously Tunable Sizes: Synthesis and Size Effects on Cellular Contrast Imaging. Chem. Mater. 2008, 20, 4411-4419.

Park et al., Magnetic Iron Oxide Nanoworms for Tumor Targeting and Imaging. Adv. Mater. 2008, 20, 1630-1635.

Wang et al., Nanoparticle-based Optical Probes for Target-Responsive DNA Structures. Gold Bull. 2008, 41, 37-41.

Nakamura et al., Synthesis, Characterization, and Biological Applications of Multifluorescent Silica Nanoparticles. Anal. Chem. 2007, 79, 6507-6514.

Gong et al., Novel Dye-embedded Core-shell Nanoparticles as Surface-enhanced Raman Scattering Tags for Immunoassay. Anal. Chim. Acta 2006 564, 151-157.

Ow et al., Bright and Stable Core-Shell Fluorescent Silica Nanoparticles. Nano Lett. 2005, 5, 13-117.

Doering and Nie, Spectroscopic Tags Using Dye-Embedded Nanoparticles and Surface-Enhanced Raman Scattering. Anal. Chem. 2003, 75, 6171-6176.

Abdukader Abdukayum, et al., Functional Near Infrared-Emitting Cr3+/Pr3+ Co-Doped Zinc Gallogermanate Persistent Luminescent Nanoparticles with Superlong Afterglow for in Vivo Targeted Bioimaging. J. Am. Chem. Soc. 2013, 135, 14125-14133. The disclosure of this reference is hereby incorporated herein in its entirety by reference.

NON-LIMITING EXAMPLES

It is to be understood that the invention is not limited in its application to the details of construction and to the arrangements of the components set forth in the following description or illustrated in the drawings. The invention is capable of other embodiments and of being practiced and carried out in various ways as described herein. Also, it is to be understood that the phraseology and terminology employed herein are for the purpose of the description and should not be regarded as limiting.

Example 1: Synthesizing Ws

CdTe QDs may be prepared as disclosed by Mikulec, Semiconductor nanocrystal colloids: manganese doped cadmium selenide, (core)shell composites for biological labeling, and highly fluorescent cadmium telluride. Ph.D. Thesis, Department of Chemistry, Massachusetts Institute of Technology, Cambridge, Mass., USA (1999). Incorporated herein in its entirety by reference.

bis(trimethylsilyl)selenide (BTS) may be synthesized as described by Drew et al., Synthesis of Nb(O2H5C7)3Y (Y=O, S and Se): crystal structure of oxotris-(tropolonato) niobium(V) monohydrate: a seven coordinate monomer containing a terminal Nb:O bond. Inorgan. Chim. Acta 118, 165-168 (1986). Incorporated herein in its entirety by reference.

QDs are precipitated by centrifuging at 6,000 g for 10 min in methanol. Precipitated CdTe QDs are dispersed in a mixture of 15 g TOPO and 5 ml TOP, and dried under vacuum at 140 ÅãC for 3 h. An over-coating stock solution may be prepared by mixing 1:1 molar stoichiometry of dimethylcadmium and BTS in TOP. While the CdTe QD solution in TOPO and TOP was vigorously stirred at 100 ÅãC, over-coating solution was added dropwise, then the mixture is stirred an additional 3 h at 100 MC. The reaction temperature is raised to 200 MC and stirring is continued until the desired wavelength is obtained by optical spectroscopy. Shell formation proceeded by fusion of small particles of CdSe onto the cores, as well as by Ostwald ripening, and required several days to complete.

Oligomeric phosphine organic coating. First, 8 g trishydroxypropylphosphine is dissolved in 20 g dimethylformamide (DMF) and stirred vigorously at room temperature. Diisocyanatohexane (4.5 g) is added dropwise and stirred for 1 d. EIA (19.4 g) is added dropwise and stirred overnight. Solvent and excess EIA are removed at 100 ÅãC under vacuum.

For cap exchange, 100 mg of precipitated QDs is mixed with 3.0 g oligomeric phosphine ligands in 10 ml tetrahydrofuran (THF) and 2 ml DMF and stirred at room temperature for 1 h; then THF and DMF are removed at 100° C. under vacuum. The resultant viscous mixture is incubated at 120° C. for 3 h and then cooled to room temperature. Next, 50 ml of 1 N NaOH is added, forming a two-phase suspension, and the solution is stirred vigorously at room temperature until only a single, slightly turbid dark brown solution is present. The solution is filtered through a 0.2-µM PTFE filter (for example, Nalgene) and then ultrafiltered with 1,000 volumes of PBS, pH 7.4, using a 50-kDa-cutoff membrane (for example, Pellicon XL, Millipore).

Example 2

A 4 year old right handed male presents with acute onset aphasia and right sided hemiplegia to the emergency department. Computed Tomography (CT Scan) without contrast identifies a left middle cerebral artery stroke. NIH stroke scale is 17. Although there are no FDA approved therapeutic interventions available to this patient, after careful risk benefit analysis, the patient is taken urgently to interventional radiology for mechanical thrombectomy and intra-arterial lytic agents within the occluded artery. Time to reperfusion is 3 hours, however, post procedure magnetic resonance perfusion identifies areas of continued perfusion mismatch and a penumbra area corresponding to the patient's language circuits. The patient shows improved strength and NIH stroke scale is now 9, however the patient remains aphasic. After reperfusion is achieved 200 µl of 2 µM of activated (by an external light/laser source) quantum dot solution (a specially coated (polydentate phosphine coating renders them soluble, disperse and stable in serum and cerebrospinal fluid) and specifically near-infrared (NIR) tuned CdTe(CdSe) core(shell) type II quantum dot (OD) nanoparticale) is injected into the previously occluded artery. After the patient is admitted to the intensive care unit a lumbar puncture (LP) is performed and a lumbar drain catheter is placed and secured. The drain is then attached to a closed circuit ultra-low pressure CSF circulation pump where an additional 200 µl of 2 µM of quantum dot solution is administered into the CSF. Encased within the ultra-low pressure CSF circulation pump is an external light/laser source (two 150-W halogen sources with 725- to 775-nm bandpass filters (Chroma), a 795-nm longpass emission filter (Chroma) with system control by LabVIEW (National Instruments).

Following 72 hours of continuous bathing of the injured brain with activated NIR QD, the expected result is that the in vivo luminescence in the NIR range, will prevent secondary oxidative damage that occurs with mitochondria following reperfusion thereby dramatically reducing neuronal death in the injured brain region and salvaging the penumbra. Rather than the expected cerebral edema that peaks at 72 hours post injury, the patient is expected to demonstrate continued improvements in the NIH stroke scale with resolution of his aphasia and only minimal focal neurological deficits. A specialized filter will be placed on the CSF circulation pump and the majority of the nanoparticles can be recovered. The few remaining nanoparticles will be biologically degraded and removed via natural biological processes.

Example 3

A newborn delivered by emergency caesarian section who has suffered severe hypoxic ischemic insult due to placental detachment is placed into a NIR incubator which baths the entire child in IR and an IR head cap is placed over the child's scalp with IR delivery focused over the open fontanels. The patient is also placed on therapeutic whole body hypothermia protocol. 200 µl of 2 µM of activated quantum dot solution is injected systemically and either extraventricular or lumbar drain is placed and closed circuit ultra-low pressure CSF circulation pump is utilized to activate an additional 200 µl of 2 µM of quantum dot solution administered into the CSF. Early developmental outcomes are expected to be better than controls and rates of cerebral palsy and end organ damage is expected to be decreased.

Example 4

A 24 year old soldier sustains head trauma and spinal cord injury in combat due to a roadside explosive device. He is evacuated to base and is given hypertonic saline to reduce cerebral edema, however, it is determined that decompressive cranectomy is recommended by neurosurgery. During the operation the brain is exposed to IR light and prior to closing, the brain is bathed in activated quantum dot solution.

After admission to the intensive care unit, LP is performed and a lumbar drain catheter is placed and secured. The drain is then attached to a closed circuit ultra-low pressure CSF circulation pump where an additional 200 µl of 2 µM of quantum dot solution is administered into the CSF. Encased within the ultra-low pressure CSF circulation pump is an external light/laser source (two 150-W halogen sources with 725- to 775-nm bandpass filters (Chroma), a 795-nm longpass emission filter (Chroma) with system control by LabVIEW (National Instruments).

Compared to controls, the patient is expected to have improvements in JFK Coma Recovery Scale-Revised (CRS-R) achieved sooner and have higher Glasgow Outcome Scale (GOS) scores. Furthermore functional outcomes per level of spinal cord injury are expected to be superior to current expectations.

All publications mentioned above are hereby specifically incorporated herein by reference in full for the teachings for which they are cited. The examples and claims of the present invention are not limiting. Having read the present disclosure, those skilled in the art will readily recognize that numerous modifications, substitutions and variations can be made to the description without substantially deviating from the invention described herein. Such modifications, substitutions and variations constitute part of the invention described herein.

We claim:

1. A method for treating a disorder of the central nervous system in a subject suffering from a central nervous system injury, such method comprising:
    a) activating synthetic, light-emitting, water soluble nanoparticles to create activated light-emitting nanoparticles; and
    b) administering to said subject a composition comprising said activated light-emitting nanoparticles;
wherein the activated light-emitting nanoparticles emit light in the infra-red or near infra-red spectrum.

2. The method of claim 1, where the disorder of the central nervous system is the result of an ischemic stroke.

3. The method of claim 1, wherein the disorder of the central nervous system is the result of an impact to the head.

4. The method of claim 1, wherein the nanoparticles are selected from the group consisting of quantum dots, silica nanoparticles, magnetic iron oxide "nanoworms," Cr3+/Pr3+ co-doped zinc gallogermanate, and gold nanoparticles.

5. A method for treating or preventing oxidative damage to mitochondria following reperfusion in a subject suffering from a central nervous system injury, such method comprising administering to said subject a composition comprising activated synthetic, light-emitting, water-soluble nanoparticles,
    wherein, synthetic, light-emitting, water-soluble nanoparticles are activated prior to administration to create said activated synthetic, light-emitting, water-soluble nanoparticles; and
    wherein said activated synthetic, light-emitting, water-soluble nanoparticles emit light in the infra-red or near infra-red spectrum.

6. The method of claim 5, where the disorder of the central nervous system is the result of an ischemic stroke.

7. The method of claim 5, wherein the disorder of the central nervous system is the result of an impact to the head.

8. The method of claim 5, wherein the nanoparticles are selected from the group consisting of quantum dots, silica nanoparticles, magnetic iron oxide "nanoworms," Cr3+/Pr3+ co-doped zinc gallogermanate, and gold nanoparticles.

* * * * *